(12) United States Patent
Hermle et al.

(10) Patent No.: US 9,638,579 B2
(45) Date of Patent: May 2, 2017

(54) METHOD AND SYSTEM FOR CHECKING THE COLOR QUALITY OF PREFORMS

(71) Applicant: Finatec Holding AG, Brügg b. Biel (CH)

(72) Inventors: Matthias Hermle, Brügg b. Biel (CH); Fridolin Maibach, Safnern (CH); Beat Schlup, Biel (CH)

(73) Assignee: FINATEC HOLDING AG, Brugg B. Biel (CH)

( * ) Notice: Subject to any disclaimer, the term of this patent is extended or adjusted under 35 U.S.C. 154(b) by 0 days.

(21) Appl. No.: 14/215,481

(22) Filed: Mar. 17, 2014

(65) Prior Publication Data
US 2014/0285805 A1 Sep. 25, 2014

(30) Foreign Application Priority Data

Mar. 22, 2013 (CH) .......................................... 650/13
Dec. 10, 2013 (CH) ........................................ 2046/13

(51) Int. Cl.
| | |
|---|---|
| *G01J 3/46* | (2006.01) |
| *G01J 3/50* | (2006.01) |
| *B29C 45/76* | (2006.01) |
| *G01N 21/90* | (2006.01) |
| *B29K 105/00* | (2006.01) |

(52) U.S. Cl.
CPC ............ *G01J 3/50* (2013.01); *B29C 45/7686* (2013.01); *G01N 21/9081* (2013.01); *B29K 2105/253* (2013.01); *B29K 2105/258* (2013.01)

(58) Field of Classification Search
CPC ..... G01J 3/50; G01N 21/9081; G01N 21/909; G01N 21/9054; B07C 5/3408; B29C 45/7686; B29K 105/253; B29K 105/258

USPC .......................................................... 356/402
See application file for complete search history.

(56) References Cited

U.S. PATENT DOCUMENTS

| | | | |
|---|---|---|---|
| 5,898,169 A | 4/1999 | Nordbryhn | |
| 6,122,062 A * | 9/2000 | Bieman | G01B 11/2527 |
| | | | 356/402 |
| 6,493,076 B1 * | 12/2002 | Laitinen | G01N 21/85 |
| | | | 250/559.45 |

(Continued)

FOREIGN PATENT DOCUMENTS

EP          1479454 A1    11/2004

OTHER PUBLICATIONS

International Search Report and Written Opinion dated Jul. 14, 2014 for PCT/EP2014/055599.

*Primary Examiner* — Hina F Ayub
(74) *Attorney, Agent, or Firm* — Abel Law Group, LLP (57) ABSTRACT

The present invention relates to a method and the corresponding system for checking the color quality of preforms (2) intended for the manufacture of containers, in particular beverage bottles, the preforms (2) being transported to a collection vessel (4) by a transport device (3), and an image of the preforms (2) being made by means of an imaging device (6) and being transmitted to a processing device for checking, in which the preforms (2) are led unsorted into the collection vessel (4) upon leaving the transport device (3), the image being made between the leaving of the transport device (3) and the collection vessel (4), and in which the image is processed by the processing device in such a way that the color quality of the preforms (2) and/or defective preforms (2) are discovered.

27 Claims, 10 Drawing Sheets

(56) References Cited

U.S. PATENT DOCUMENTS

| | | | |
|---|---|---|---|
| 6,914,678 B1 | 7/2005 | Ulrichsen et al. | |
| 7,119,930 B1 * | 10/2006 | Carstensen | H04N 5/2256 |
| | | | 250/201.3 |
| 2006/0219609 A1 * | 10/2006 | Canepa | 209/552 |
| 2008/0310701 A1 * | 12/2008 | Caroli | G01B 11/25 |
| | | | 382/141 |
| 2013/0056398 A1 * | 3/2013 | Adams | B07C 5/342 |
| | | | 209/587 |
| 2013/0144431 A1 * | 6/2013 | Tidhar | B65B 5/103 |
| | | | 700/231 |

* cited by examiner

METHOD AND SYSTEM FOR CHECKING THE COLOR QUALITY OF PREFORMS

TECHNICAL FIELD OF THE INVENTION

The present invention relates to a method and a corresponding system for checking the color quality of preforms intended for the manufacture of containers, in particular beverage bottles. In particular the present invention relates to a method and a corresponding system for checking the color quality of preforms, in which the preforms are transported by a transport device into a collection vessel by a transport device, and an image being made of the preforms by means of an imaging device and being transmitted to a processing device for checking.

It should be mentioned here that the term "preform", used in the following, is not to be understood in a limiting way. In particular this term covers all pieces used for the manufacture of containers, for instance beverage bottles, but also all similar objects the production methods for which or respectively the structure and/or appearance of which are similar to the conventional preforms. Examples of such objects include in particular syringes (for medical or laboratory use), test tubes, cuvettes, etc. It is also possible to use this invention in the same way with other products, e.g. with plastic caps, among other things.

STATE OF THE ART

In the manufacture of containers, in particular beverage bottles, first used generally are so-called preforms, i.e. premoldings or blanks, and these preforms are then further processed into finished containers. These preforms are typically made of plastic, above all PET (polyethylene terephthalate). Other, similar articles, such as the above-mentioned syringes, test tubes, cuvettes, etc. but also plastic caps, among other things, are made in a similar way.

Because manufacturing processes are energy-intensive and because, as a rule, the manufacturing processes have to be stopped upon discovery of preforms that are not flawless (incurring higher costs), manufactured preforms as well as other mentioned preform-like articles are checked as a rule before they are sent to further processing. Possible defects in the manufactured preforms are above all imprecise dimensions, irregular shape, too thin or too thick wall areas, pin holes, burns, presence of foreign bodies and/or bubbles, but also deficient color quality.

Various systems and methods are known for checking preforms for these defects. In particular checking with the aid of digital imaging devices has become established. Preforms are thereby led past an imaging device so that one or more images of each preform are able to be made. An electronic processing device compares the images made with a reference image and determines whether it has certain defects. Reference values relating to non-conformance with quality standards lead to the elimination of the preform.

Common to all the previously known systems or respectively methods is that the objects to be checked have to be arranged and aligned so that the images of each object are able to be made in the desired position. In this way defects can be discovered very accurately and quickly. However this means that the examination of the objects to be checked cannot be carried out already in the manufacturing machine, but instead a separate checking system is always necessary downstream from the manufacturing machine. This once again means that the installation and the interface between the two systems are complex, and that they are only able to be achieved using qualified personnel. Moreover such checking systems require additional space, which is not always available with existing manufacturing machines.

DISCLOSURE OF INVENTION

Thus the object of the invention is to propose a method of checking the color quality of preforms as well as a system suitable for carrying out this method, in which the above-described drawbacks of the known methods and systems are completely overcome or at least greatly diminished.

In particular an object of the invention is to propose a method and the corresponding system for checking the color quality of preforms, thanks to which a reliable, quick and very easy automated checking of the color quality of a preform series is ensured with very little space requirements. Moreover the installation of this system should be able to be carried out very simply also on the existing manufacturing machines.

According to the present invention these objects are achieved in particular through the elements of the two independent claims. Further advantageous embodiments follow moreover from the dependent claims and the description.

In particular these objects of the invention are achieved in that, in the method of checking the color quality of preforms intended for the manufacture of containers, in particular beverage bottles, the preforms being transported by a transport device into a collection vessel, and an image of the preforms being made by an imaging device and being transmitted to a processing device for checking, the preforms are led in an unordered way into a collection vessel upon leaving the transport device, the image being made between the leaving of the transport device and the collection vessel, and the image being processed by the processing device in such a way that the color quality of the preforms is checked and/or defective preforms discovered.

Understood by unordered is thereby, for the time being, any type of order such as, for instance, the spacing to individual preforms with respect to one another and the alignment of the preforms in two-dimensional or three-dimensional space. Also to be understood as unordered is when the preforms have an irregular alignment to one another in one direction only.

The advantage of this invention lies in particular in the defective preforms being able to be discovered very simply, also in particular without their having to be specially aligned. Moreover hardly any adaptation to the existing facilities for preforms is required.

In one embodiment of this invention, the preforms are led in free fall into the collection device after leaving the transport device. This embodiment of this invention has inter alia the advantage that no additional feed devices have to be provided. Moreover the preforms can be received completely without their being partially or completely covered by any delivery devices.

In another embodiment of this invention the image of the preforms is made in front of a projection screen or a plate. The advantage of this embodiment is that the background in the pictures is able to be designed as individually so that an optimal evaluation is possible. In practice, undesired flaws owing to irrelevant elements can be completely excluded thanks to this embodiment.

Preferably the projection screen or the plate have a color having a good contrast to the color of the preforms. A good contrast is present if the colors of the preforms and of projection screen or plate are differ sufficiently so that a clear determination can be made about the color quality of the preforms or defects can be recognized. Concretely, the color of the plate can be white in many cases, but also other colors (such as black, for example) are absolutely conceivable. Likewise it is easily possible to take a metal-colored plate (e.g. stainless steel color). Thanks to the good contrast between the colors of the preforms and the color of the projection screen, or respectively of the plate, preforms are able to be especially well identified in the pictures taken, which leads to a better and faster evaluation of the image.

On the other hand it is also possible to use an at least partially transparent projection screen or respectively plate. For example, a glass window can be provided in such a non-transparent projection screen or respectively plate. The advantage of such a projection screen or respectively plate is the possibility of adapting the background of the images. Moreover the transparent area of the projection screen or respectively plate is able to be used for illumination of the preforms.

In still another embodiment of this invention attachment means are provided, thanks to which the projection screen, or respectively plate, can be positioned. This embodiment of the present invention has in particular the advantage that the projection screen or respectively plate (i.e. in particular also the inclination with respect to the perpendicular, as will be explained in the following) can also be adjusted depending upon the position of the imaging device in order to be able to ensure an optimal evaluation of the pictures taken.

In still another embodiment of the present invention, pluralities of images are evaluated in order to determine a flawless series of preforms. The advantage of this embodiment is that a statistically relevant number of pictures may be taken before a defect is determined. A certain tolerance in the evaluation can thereby be taken into account.

In another embodiment of this invention, the preforms are illuminated by means of at least one lighting fixture when making the image. The advantage of this embodiment is above all that when taking the pictures of the preforms to be checked a sufficient illumination of the preforms may be ensured. A good picture quality can thereby be guaranteed, which leads to a better evaluation of the images.

Preferably the at least one lighting fixture is positioned behind the projection screen or respectively the plate so that the preforms are illuminated from behind with respect to the imaging direction. Thanks to an illumination from behind (in relation to the direction of view of the imaging device) the preforms can be well illuminated, whereby the various deficiencies may also be detected much more easily and much more precisely. To this end the lighting fixture can be disposed advantageously behind the transparent region of the projection screen or respectively plate.

In another embodiment of the present invention, preforms slide over the plate, after leaving the transport device, in such a way that they are led into the collection vessel. Thanks to this plate the preforms can be channeled, on the one hand, and, on the other hand, they can be brought into one plane, it being possible for them to continue to be unordered in this plane. They can e.g. be e.g. at different spacings or in different alignment. This embodiment of the present invention has inter alia the advantage that the preforms are positioned optimally with respect to the imaging device, without special alignment devices having to be used. The preforms are aligned at a defined spacing to the imaging device. Moreover this plate also serves as the background in the pictures, as described above, so that an optimal evaluation of the image is made possible.

In another variant of the present invention the plate is perforated and is designed, for example, as a perforated plate. The use of such a plate has the advantage that the weight of the plate and of the entire facility can be reduced without the functionality of the plate becoming lost.

In a further variant of the present invention at least a portion of the plate is curved at least in one direction. For example, the curvature can extend transversely to the direction of the sliding of the preforms. Preferably it is possible for the plate to be curved in such a way that at least one channel is formed for the sliding preforms. In this way the sliding characteristics of the preforms may be better influenced, and it can be ensured that all preforms slide over a certain region of the plate. It is thereby possible to configure the taking of the picture of the sliding preforms more precisely since the distribution of the preforms in front of the imaging device can be limited in a further dimension. Thus with a channel-shaped plate the sliding preforms can be partially ordered so that the evaluation of the images can be made in a simpler and faster way.

It should still be mentioned here that, in addition to the above-described method of checking the color quality of preforms, the present invention also relates to a corresponding system.

The invention has been presented with reference to a plurality of embodiments. The individual technical features of one embodiment can by all means be also used in combination with another embodiment with the presented advantages. The description of the inventive technical features are therefore not limited to the respective embodiment.

BRIEF DESCRIPTION OF THE DRAWINGS

Embodiments of the present invention will be described in the following with reference to examples. The examples of the embodiments are illustrated by the following attached figures.

DETAILED DESCRIPTION OF THE EMBODIMENTS

Figure 1:
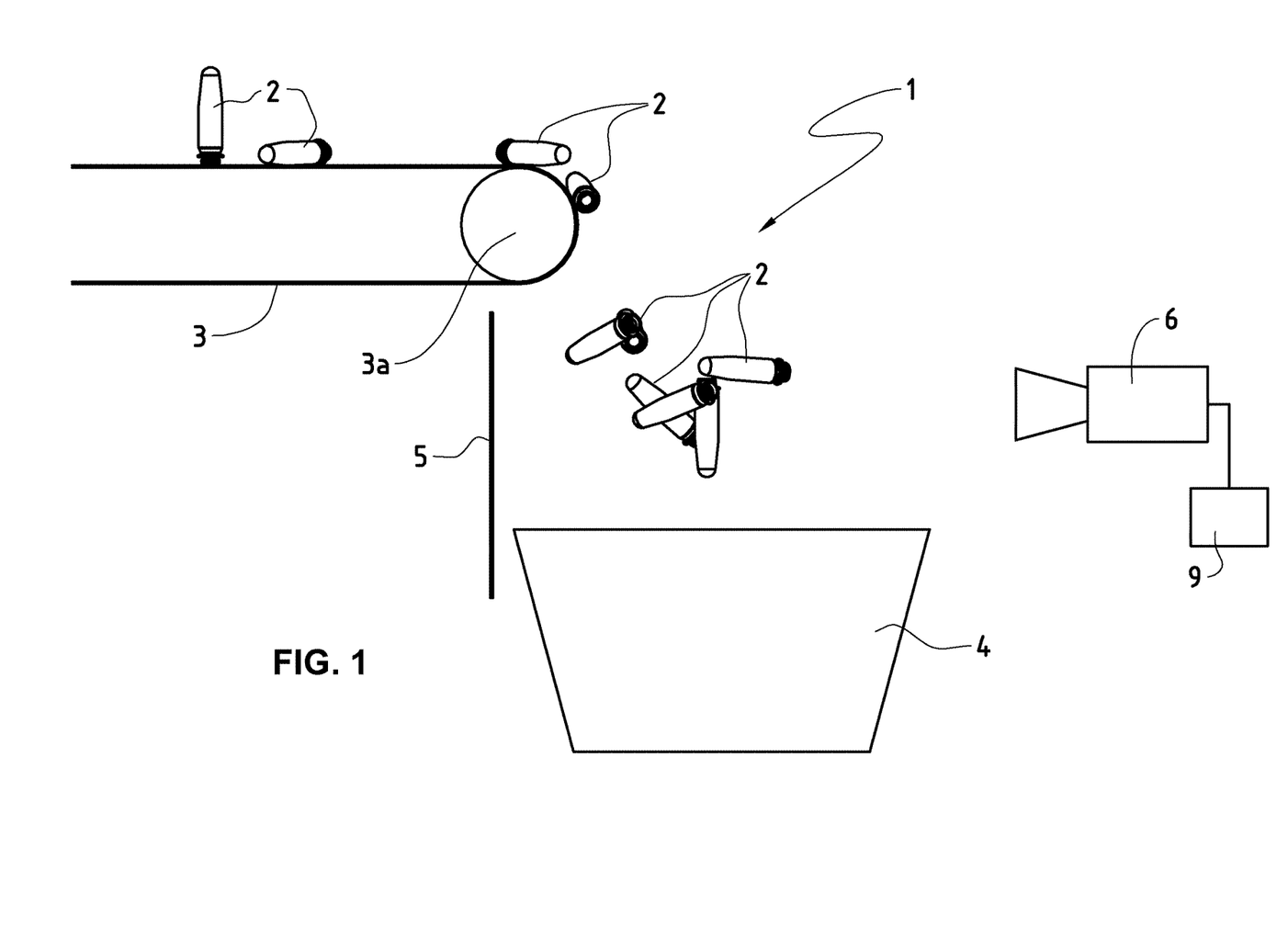
FIG. 1 shows schematically a lateral view of a system for checking the color quality of preforms according to a first embodiment of the present invention.
Figure 2:
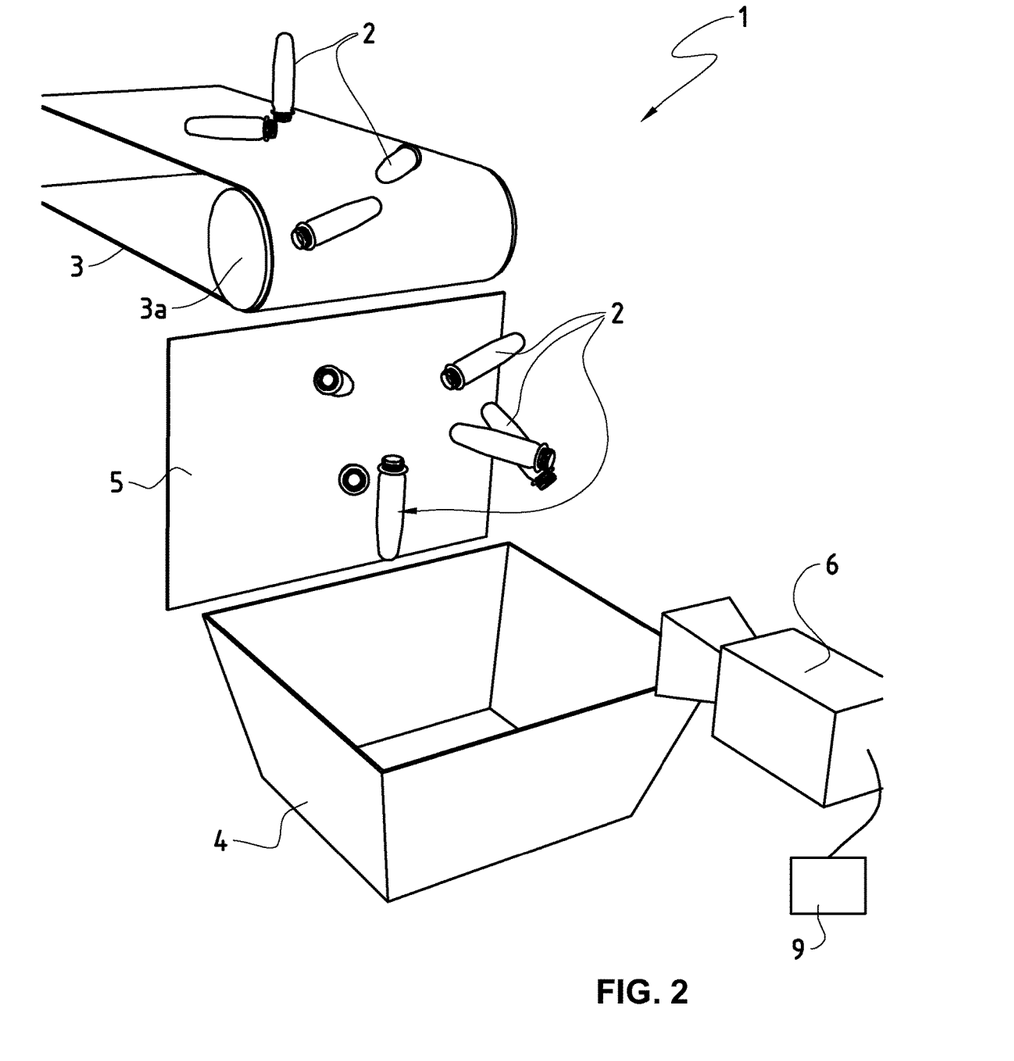
FIG. 2 shows the system illustrated in FIG. 1 for checking the color quality of preforms in a view in perspective from the front.

Illustrated in FIG. 1 and FIG. 2 is schematically a first embodiment of a system 1 for checking the color quality of preforms according to one embodiment of the present invention.

The preforms 2 produced in a conventional manufacturing machine or respectively in a conventional manufacturing system of plastic (e.g. PET) are transported unordered by the transport device 3 to a collection vessel 4. Understood by the term unordered should be an arrangement of preforms that results "naturally", i.e. without a previous ordering or respectively sorting. Of course it is also conceivable that the preforms 2 are passed on by the transport device not to a collection vessel 4, but to a further transport device. However the present invention also works the same way also in this alternative case. The transport device 3 in FIGS. 1 and 2 is a conventional conveyor belt with a drive roller 3a, which is driven via a drive (not shown). It is however conceivable of course to use another suitable transport device, for example a vacuum system or a gripping device.

After leaving the transport device 3 the transported preforms 2 reach a collection vessel 4 (indicated schematically). The collection vessel 4 can thereby be a simple cardboard box that is closed by the operating personnel after being filled and is carried away, or a more complex collection vessel, however, that can be used automatically or semi-automatically for packaging and storage of preforms 2. Instead of the collection vessel 2 a further conveyor belt, a so-called cooling belt or another similar device can be foreseen. This is then used in particular when the examined preforms 2 must be subjected to another check and/or treatment.

As can be seen very well with reference to FIGS. 1 and 2 the preforms 2 are unordered during transport on the conveyor belt 3 as well as during the entry into the collection vessel 4. In other words, the preforms 2 are brought directly out of the manufacturing machine with an alignment or an ordering onto the conveyor belt and in this state are transported to the collection vessel 4. However, if the preforms 2 happen to come out of the manufacturing machine in an ordered way then it could also occur that they are also transported on the conveyor belt also in this ordered way. Clearly the present invention would also function in such a situation flawlessly, but it is in no way dependent upon such an alignment or respectively ordering.

Shown on the right-hand side in FIG. 1 or respectively in FIG. 2 is an imaging system 6. This can be a very conventional digital camera, for instance, but the invention is not limited thereto, and one skilled in the art will readily know other imaging systems that can be used instead of the conventional digital camera. The imaging system 6 is connected to a processing unit 9 (i.e., a computer).

The preforms 2 transported generally unordered on the transport device 3 leave this transport device 3 likewise in an unordered way and then fall (through the effect of gravity) into the collection vessel 4. At this moment, i.e. precisely between leaving the transport device 3 and falling into the collection vessel 4 an image is made in each case of the preforms 2 falling past by the imaging system 6 and is transmitted to the processing device 9 (i.e., a computer) for checking. It is also conceivable for a series of several pictures to be made instead of a single image, so that in each case the taken picture for checking can be selected, in which at least one representative number of imaged preforms 2 to be checked has the optimal position. On the basis of this representative number then a determination may be made with respect to the total number of preforms.

In the first embodiment shown in FIGS. 1 and 2 a projection screen or respectively a screen device can be provided behind the falling preforms 2 (seen from the viewpoint of the imaging system 6), the function of which will be explained later. However it is also conceivable to achieve this first embodiment of the invention without the projection screen 5.

Figure 3:
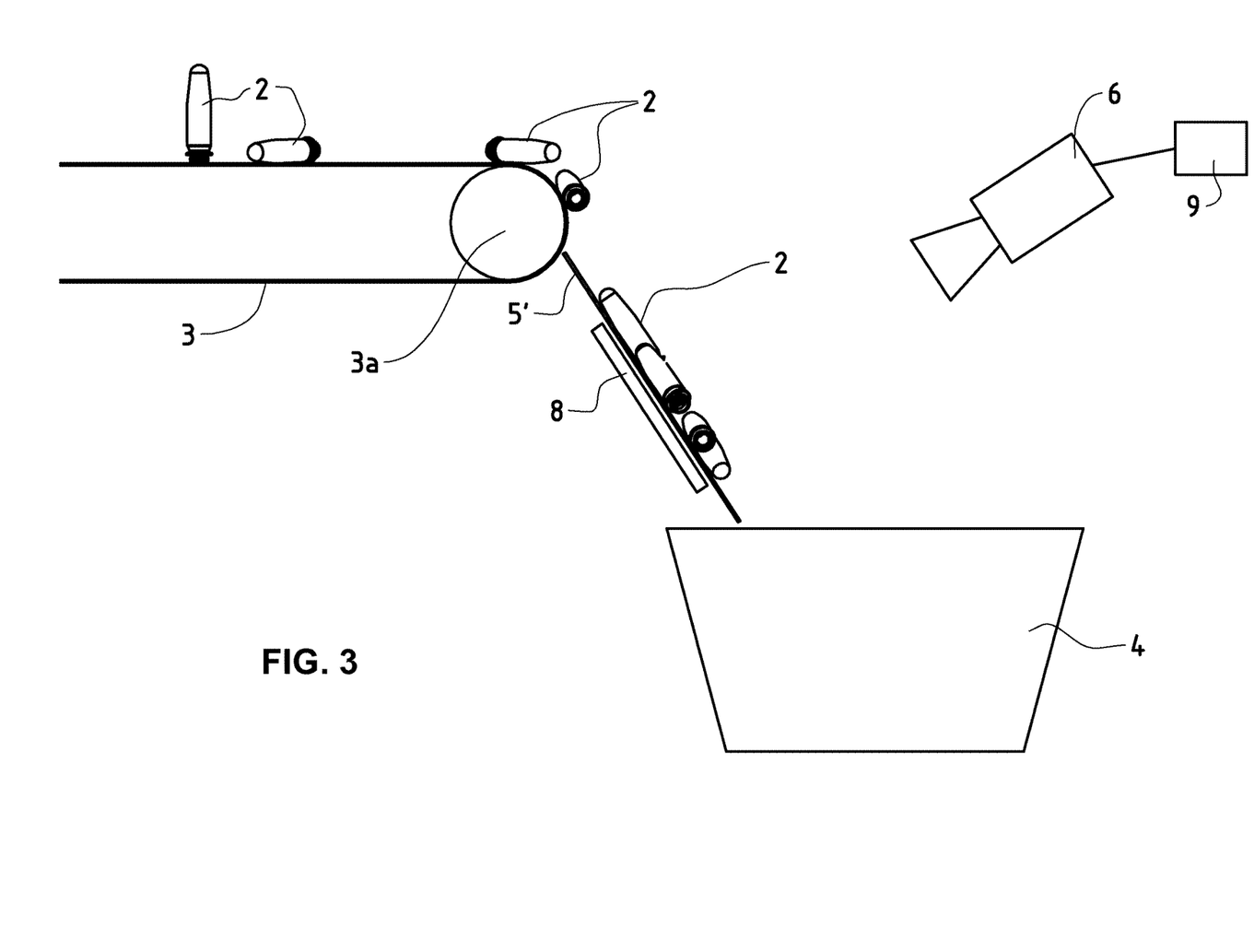
FIG. 3 shows schematically a lateral view of a system for checking the color quality of preforms according to a second embodiment of the present invention.
Figure 4:
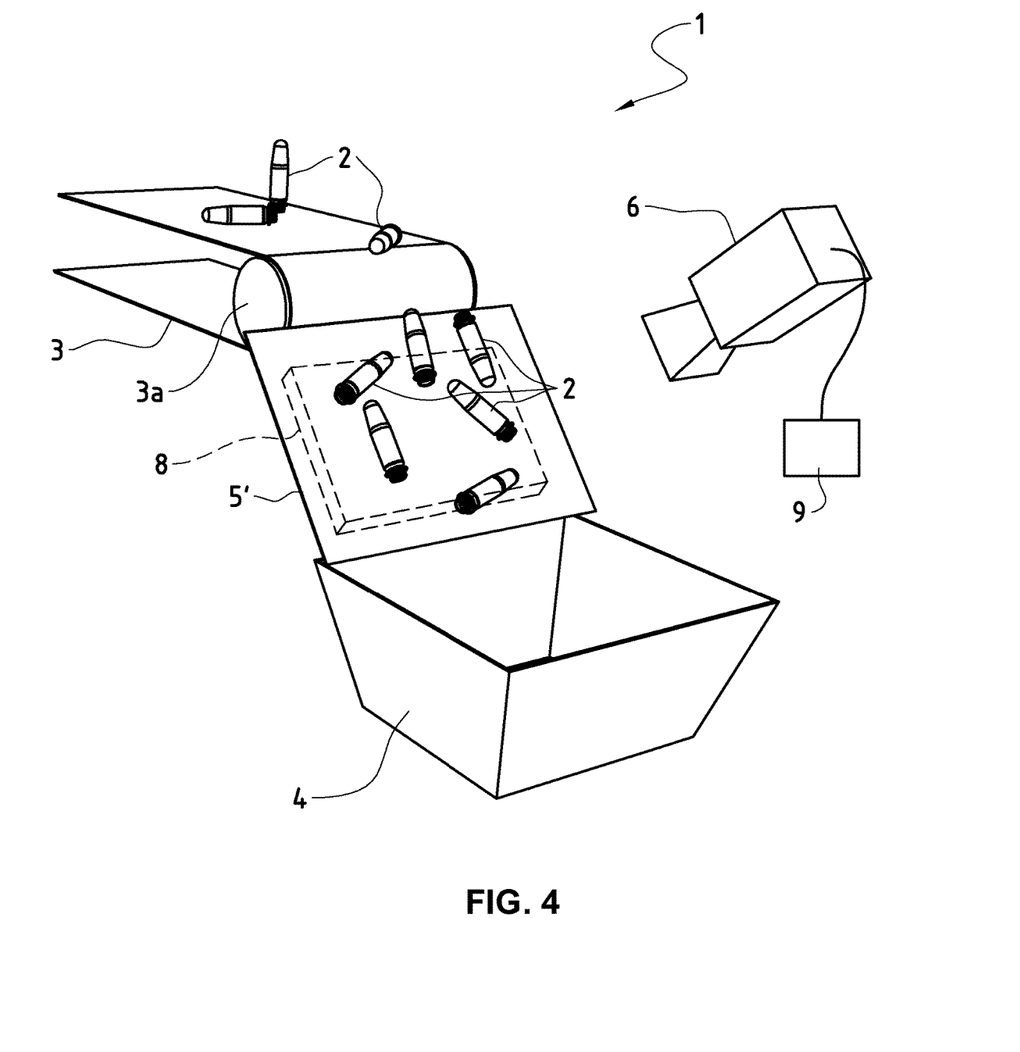
FIG. 4 shows the system illustrated in FIG. 2 for checking the color quality of preforms in a view in perspective from the front.

Illustrated in FIG. 3 and FIG. 4 is schematically a system 1 for checking the color quality of preforms according to a second embodiment of the present invention. Same parts and installations corresponding to those of the first embodiment and having the same function are accorded the same reference numerals.

The preforms 2 transported basically in an unordered way on the transport device 3 leave this transport device 3 likewise in an unordered fashion and then reach a plate 5', over which they are able to slide (in particular through the influence of gravity), in order to be introduced into the collection vessel 4. During the sliding on the plate 5' the preforms 2 are also unordered, but all are situated in one plane of the plate 5'. Thus during the sliding on the plate 5', i.e. between leaving the transport device 3 and falling into the collection vessel 4 an image is made in each case of the preforms falling past by the imaging system 6 and is transmitted to the processing device. It is also conceivable to do a plurality of pictures instead of a single image so that in each case that taken image may be selected for checking in which the imaged preforms 2 to be checked have the optimal position.

Figure 5A:
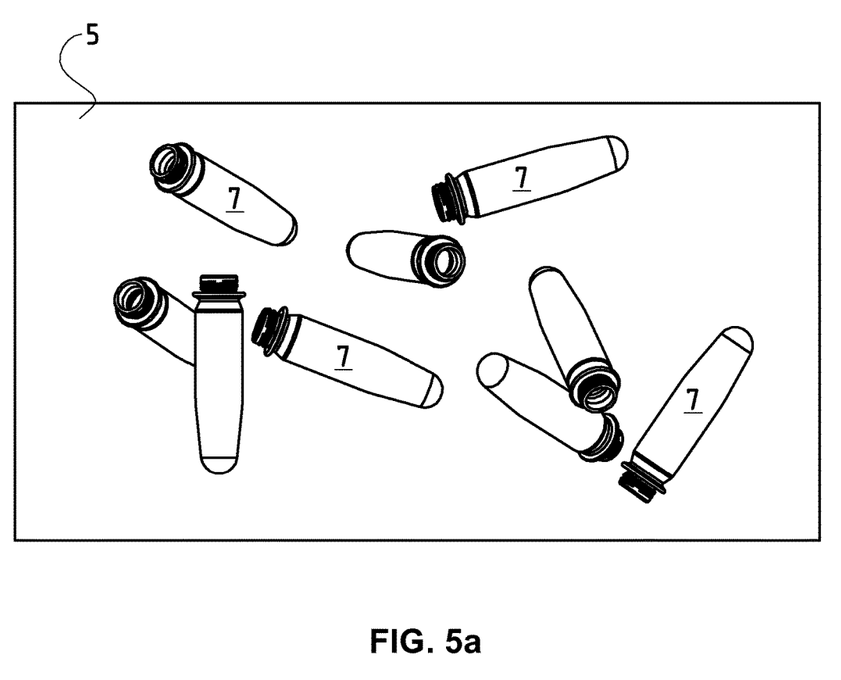
FIGS. 5a and 5b show schematically a representation of a possible image, made for checking the color quality of preforms by an imaging system in the system of FIG. 1 or respectively FIG. 3 and evaluated by a processing unit.
Figure 5B:
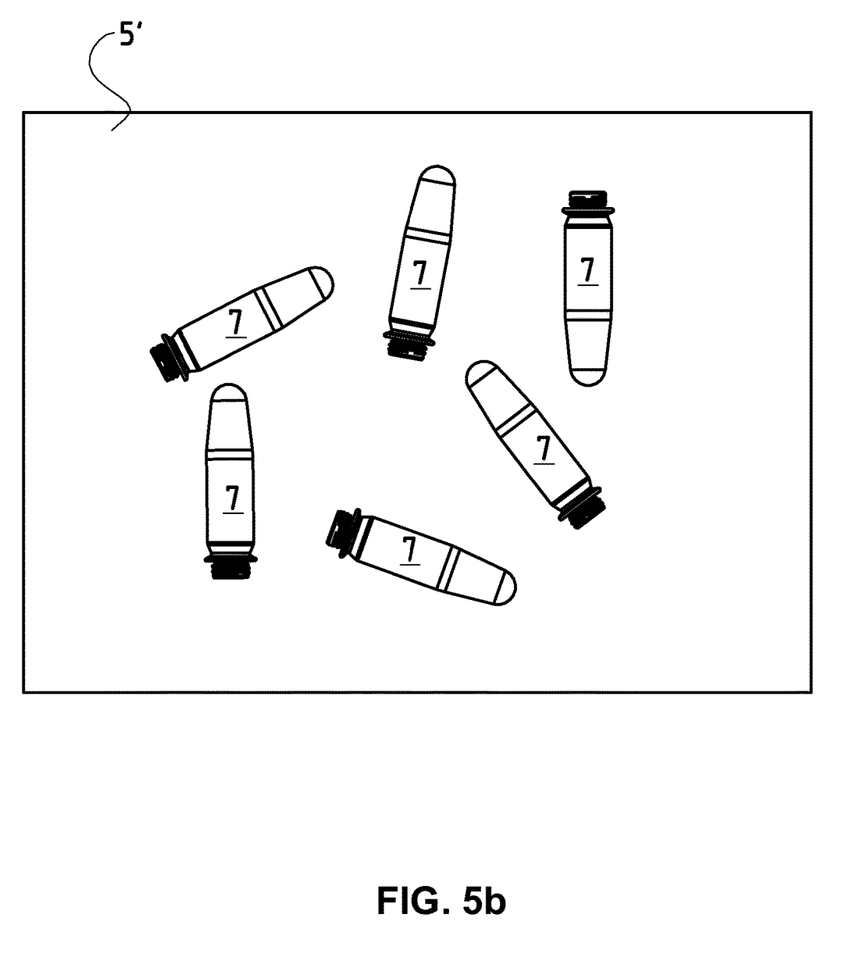

One image is illustrated schematically in FIGS. 5a and 5b made with the system according to the first or respectively second embodiment of the invention. Images of a plurality of preforms may be identified in this picture. The projection screen can be seen in FIG. 5a, and the plate 5' in FIG. 5b, in the background of the picture. In FIGS. 5a and 5b the images of preforms bear the reference number 7 (instead of 2) so that they are able to be distinguished from the "genuine" preforms. In other words, the preforms designated by 7 represent preforms that are representative for all preforms. The preforms 7 are in an area in front of the projection screen 5 that is suitable for obtaining images suitable for evaluation using the processing device 9 (i.e., a computer). The area is defined e.g. by a spacing to the imaging system 6.

In the image, given by way of example, according to FIG. 5a it can be seen that the preforms 7 are unordered. In this sense the image of certain preforms 7 is incomplete under certain circumstances, since they are completely or partially covered by other preforms 7. Moreover it can be seen that some preforms 7 in the picture taken are at an angle with respect to the projection screen 5 (or respectively with respect to the plane that is perpendicular to the angle of view of the imaging system 6) whereby one portion of their surface can be seen in the picture. In an extreme case it is conceivable that during free fall a preform 7 is located exactly in the angle of view of the imaging system 6. In this situation only the image of the preform head or respectively of the preform floor would be able to be seen in the corresponding picture.

As can be seen in FIG. 5b, in the case of a plate 5', all preforms 7 lie in the same plane, i.e. in the plane of the plate 5', so that they are always situated at an optimal angle with respect to the imaging system 6. It can thereby be guaranteed that a large number of pictures taken of the preforms 7 can be used for evaluation.

The projection screen 5 can be made up of various materials, for instance plastic or textile. The plate 5' can likewise be composed of many materials, for example plastic, glass or metal, but also of a combination of materials.

Preferably the projection screen 5 and the plate 5' have a color such that a good contrast to the color of the preforms results. White is a good choice for many preform colors, but it is also conceivable also to use other colors, such as for instance black (for the checking of yellow preforms 2). A metal-colored projection screen or plate 5' (e.g. of stainless steel) is also conceivable. Moreover the projection screen 5 or plate 5' can also be designed at least partially transparent, for example in that it has a transparent area (in a manner of speaking a window). This transparent area can be made in a metal plate, for example, but other variants are absolutely conceivable. Finally the plate 5' can also be perforated, or consist of a perforated sheet.

For attachment or respectively correct positioning of the projection screen 5 or plate 5' special attachment means can be foreseen (not shown), for example frames or hanging hooks. In particular it is possible and advantageous to provide such attachment means with which the plate 5' can be attached directly to the transport device 3.

Visible in FIGS. 3 and 4 is also a lighting body 8 behind the plate 5'. It is practical if the lighting body 8 is positioned in such a way that the preforms 2 sliding on the plate 5' are illuminated through the transparent area of the plate 5'. Thanks to the lighting body 8, preforms 1 can be illuminated from behind in relation to the imaging system 6 in any case. Such a lighting body 8 is likewise conceivable for an embodiment with a projection screen 5.

The images made are transmitted from the imaging system 6 to the processing device 9. The images for checking the color quality of preforms are subsequently evaluated by this processing unit 9 (i.e., a computer). Concretely, in each evaluated image, first one or more preforms 7 are identified which were aligned during taking of the picture such that their whole length may be seen completely as completely as possible. These preforms 7 can be compared, for example, with a reference image of a correct preform in order to check the color quality of the preform 7 to be imaged. Thus, according to the invention, the correctly situated preforms with respect to position, angular position, overlapping parts, etc. are automatically detected in the picture taken so that they are each able to be compared with a reference image.

In the case of the first embodiment with a projection screen, e.g. those preforms are identified which, in free fall and during the taking of the picture were aligned at a certain direction with respect to the projection screen that their entire length in the image can be seen as completely as possible. Concretely it can be said that those preforms 7 are to be identified the longitudinal axis of which (at the moment of taking the picture) is situated at least parallel to the projection screen 5. In FIG. 5a the preforms having the reference numerals could be searched for.

In the case of the second embodiment with a plate 5' those preforms are identified which are completely imaged, i.e. which lie completely covered in the picture region and are not covered by other preforms. With deviations from the reference picture (e.g. in the case of too great or too weak a coloring of the preform 7) a defective color of the preform can be directly detected. Instead of a reference picture in the narrower sense, it is also conceivable to use certain characteristic reference values, which, with the imaged preforms to be checked, are then compared with respect to the corresponding measurement results.

This method makes it possible, depending on the circumstances, not to subject all preforms 7 to examination since, seen statistically, there can also be such preforms 2 that during sliding are situated in such a way between the transport device 3 and the collection vessel 4 that their image cannot be very well evaluated in the described way. In an extreme case it is moreover thoroughly conceivable that no single image of preforms 2 is aligned in one picture such that its evaluation is possible by the processing device. Nevertheless these drawbacks can be taken into account since the color quality of all preforms 2 in the same series are normally identical or nearly identical so that the evaluation of a certain number of preforms 7 is completely sufficient in order to be able to determine the color quality of the whole series.

In this connection it is also thoroughly conceivable that the evaluation of each image is used directly in order to decide upon the color quality of a preform series. On the other hand it is also thoroughly possible that first a multiplicity of taken pictures must be evaluated before a conclusion about the color quality of the entire series may be made. Moreover it should be mentioned here that thanks to the present invention not only deficiencies in the color quality of preforms are able to be detected, but also many other possible defects, such as air bubbles, burns, soiling and the like. Thus the present description of the invention should not be interpreted in a limiting way.

According to the invention, it is moreover possible to offer the imaging system 6, the respective processing device, the projection screen 5 or respectively the plate and the corresponding attachment means in each case together as a kit. In this case these elements could be installed by a person not specifically trained on a conventional manufacturing machine or respectively on a conventional manufacturing machine for preforms in a simple way and could be put into operation. Thanks to this possibility no adaptations in the manufacturing machine itself would have to be carried out.

Shown in FIGS. 6 to 9 are a second and a third variant of the system according to the second embodiment of the present invention. The 4 systems according to the present invention differ from the system illustrated in FIGS. 3 and 4 only in that the plate 5', via which the preforms 2 slide after leaving the transport device 3 and before entry into the collection vessel 4, are not designed flat. For this reason the elements in FIGS. 6 to 9 bear the same reference numerals as the elements in FIGS. 1 to 4.

Concretely the plate 5' in the system according to the second variant of the invention (FIGS. 6 and 7) is curved in such a way that it is designed channel-like or trough-like. As can be seen very well in FIG. 6, the plate 5' has a shape making it possible in principle for all preforms 2 during the sliding to collect in the middle of the plate 5' and the plate 5' to be left in the middle of the lower rim. In this way the position or respectively the focus of the imaging system 6 may be adapted so that the pictures of the sliding preforms 2 are able to be made in an optimal way. Also the sliding performs 2 are partially sorted owing to the curved shape of the plate 5', i.e. they align themselves necessarily in such a way that their longitudinal axes are disposed parallel to the direction of slide. Also this fact contributes to the taking of the pictures of the preforms 2 to be evaluated and their evaluation being able to be optimized. At the same time the preforms are unordered such that different spacings may arise or the preforms may have a surface in opposite directions.

Figure 6:
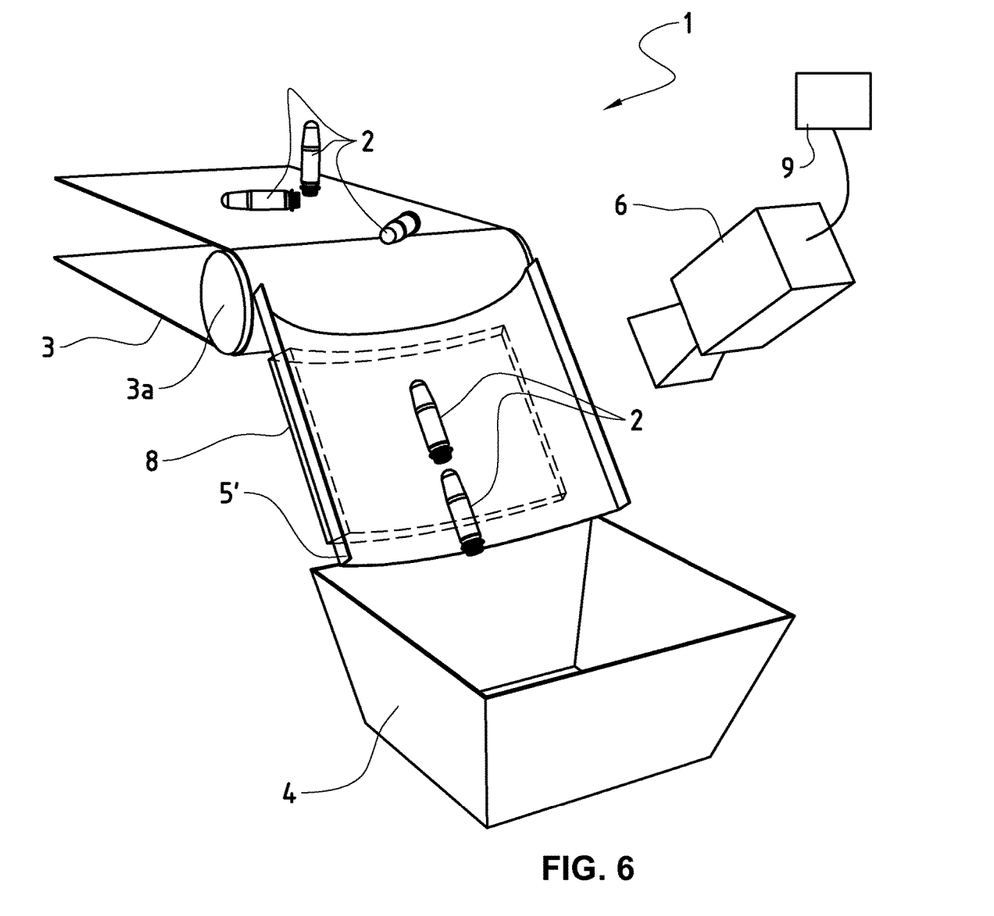
FIG. 6 shows schematically a view in perspective from the front of a system for checking the color quality of preforms according to another variant of the second embodiment of the present invention.
Figure 7:
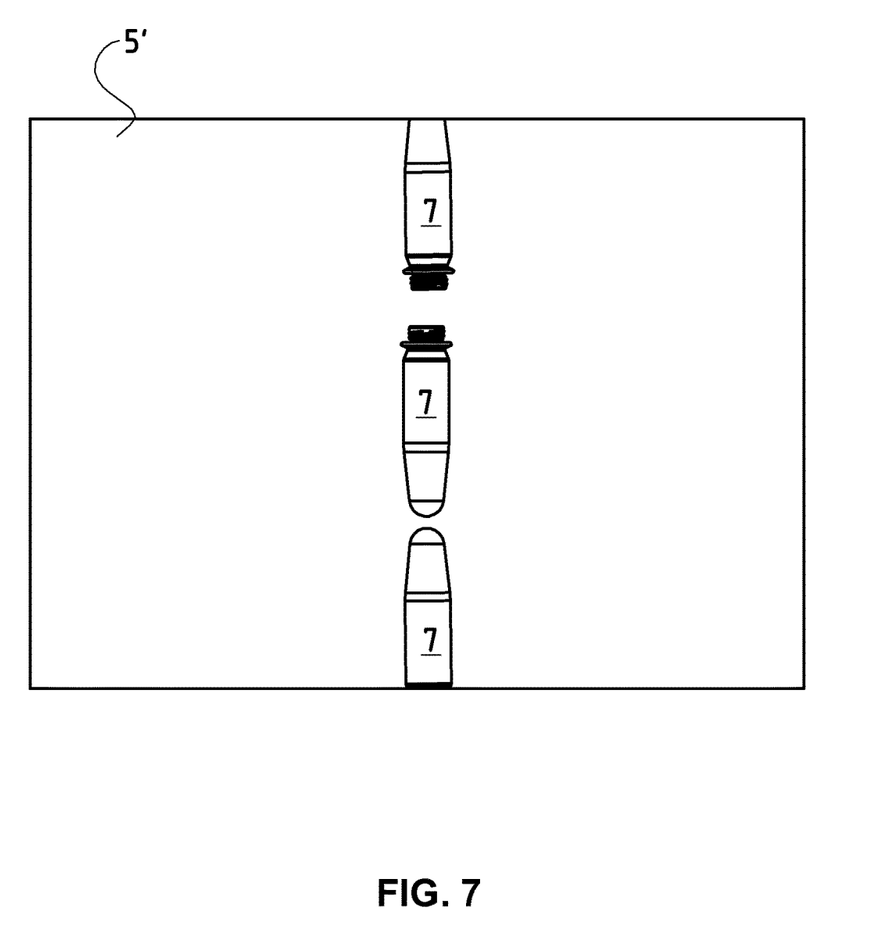
FIG. 7 shows schematically a representation of a possible image for checking the color quality of preforms by an imaging system in the system of FIG. 6 and evaluated by a processing unit.

Of course it is also conceivable for the curvature of the plate to be disposed or respectively designed in a different way, as is shown in FIG. 6. One skilled in the art will however know how the curvature of the plate 5' may be adapted to the special requirements.

Figure 8:
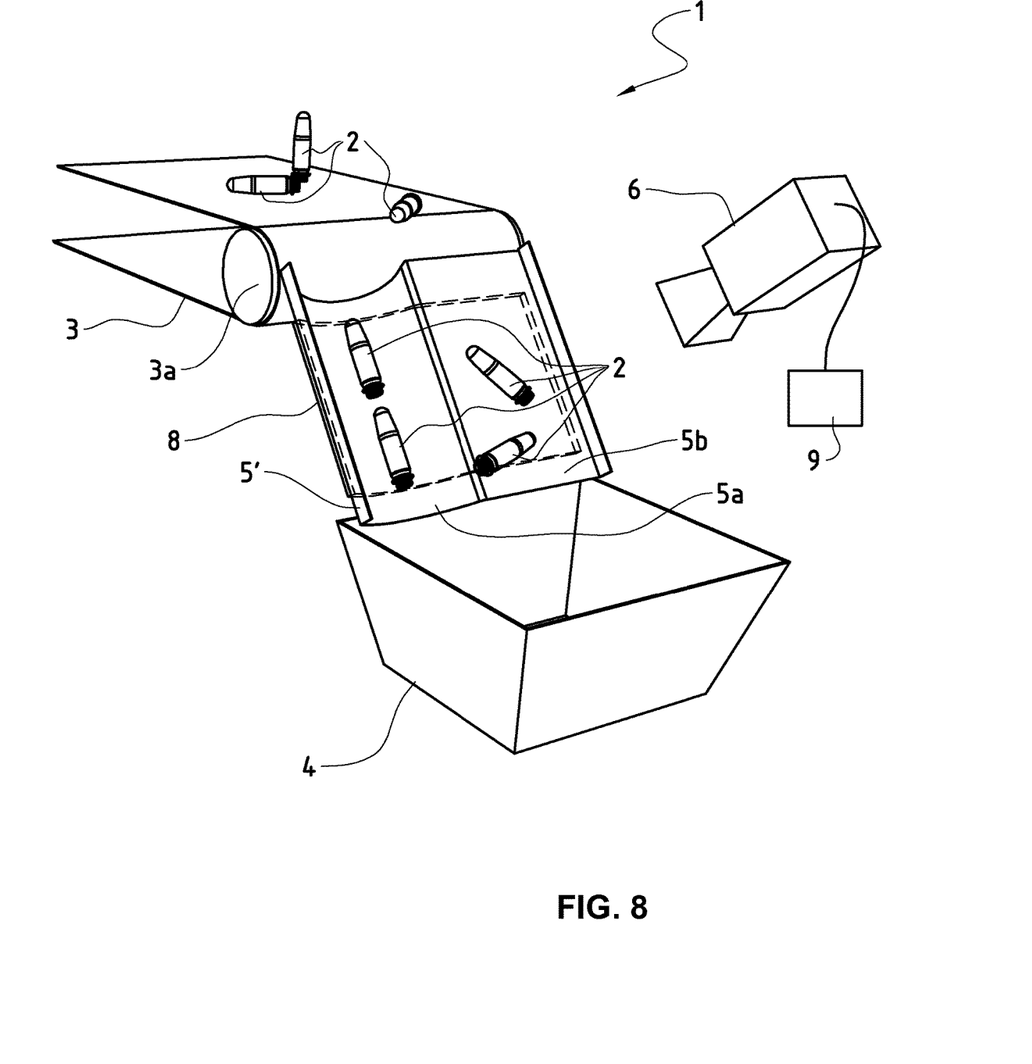
FIG. 8 shows schematically a view in perspective from the front of a system for checking the color quality of preforms according to still another variant of the second embodiment of the present invention.
Figure 9:
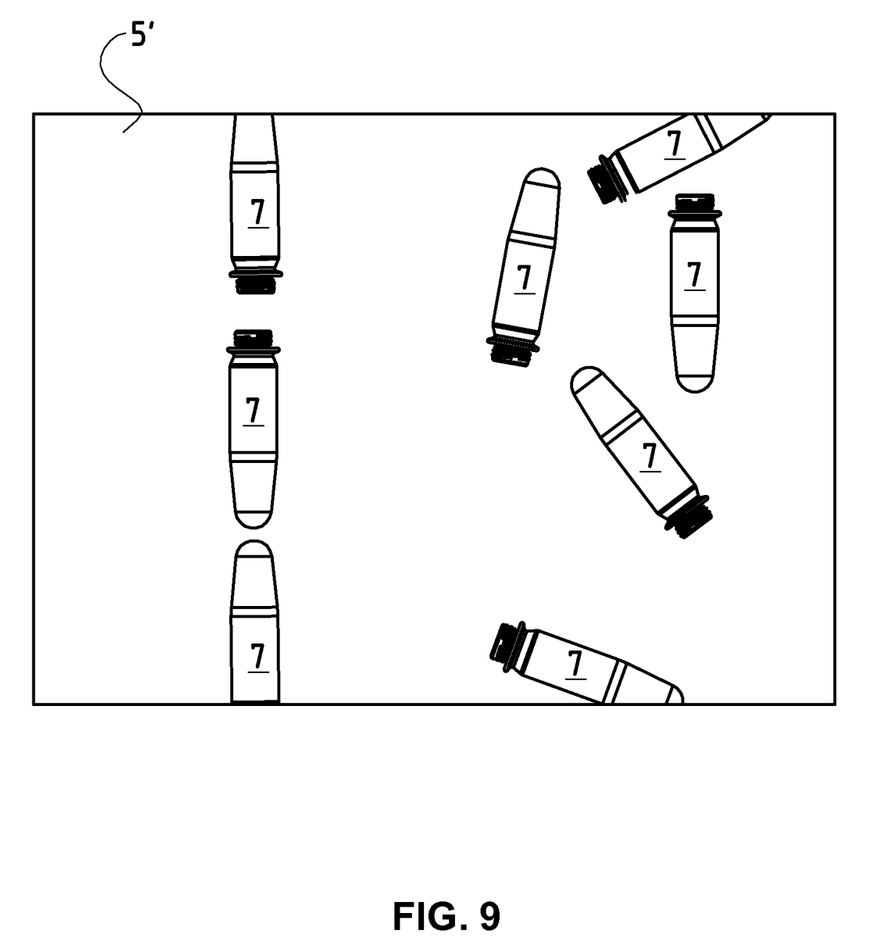
FIG. 9 shows schematically a representation of a possible image for checking the color quality of preforms made by an imaging system in the system of FIG. 8 and evaluated by a processing unit.

In particular it is also conceivable that not the entire plate 5' has a curvature. Such a variant is shown in FIGS. 8 and 9. In contrast to the variant shown in FIGS. 6 and 7, the plate 5' in FIG. 8 has a curved area 5a and a flat area 5b. With this variant, the advantages of the systems according to the first embodiment (FIGS. 1 and 2) and the second embodiment (FIGS. 3 and 4) of the present invention may be combined. With this variant it is thus especially advantageous if two imaging systems 6 are provided, each making images of preforms 2 in one of the two areas 5a and 5b of the plate 5'. Such a double configuration is also possible however in other cases.

Moreover it would be possible in still another embodiment of the present invention for images of the preforms 2 to be made by the imaging system 6 not just before leaving the transport device 3 (thus while the preforms 2 are in free fall), but beforehand, still during transport of the preform on the transport device 3). For this purpose the imaging system 6 can be disposed over the transport device 3, so that it is directed on the upper side of the transport device 3. Images of the preforms 2 transported on the transport device 3 can then be made by the transport device being deigned completely or partially transparent so that a sufficient illumination of the preforms 2 is possible. The pictures of the preforms 2 taken in this way correspond substantially to the images taken with or without projection screen 5 in free fall or the pictures taken during the sliding on the plate 5' so that the subsequent evaluation may be carried out in the same way.

It should be mentioned here that the present invention is not limited to the embodiment described. It will be clear to one skilled in the art that further developments and changes within the scope of the protected invention are easily possible. Thus, for example, system elements may be replaced, as needed, by other elements fulfilling the same (or similar) functions. It is also conceivable for the following method or respectively the following system to be used not exclusively for checking the color quality of preforms, but to check any other qualities. Likewise additional devices and/or elements could be provided, for example a multiplicity of imaging devices could be provided by means of which the preforms 2 to be checked may be imaged from different sides. Such measures and adaptations come however within the scope of protection of the invention defined by the following claims.

The invention claimed is:

1. A method of checking the color quality of manufactured bottle preforms, comprising:
   transporting the preforms by a transport device toward a collection vessel;
   leading the preforms in an unsorted way into the collection vessel upon leaving the transport device such that the preforms are sliding on a slide or in free-fall;
   forming an image of the preforms by an imaging device, wherein the image is made as the preforms are lead in the unsorted way upon leaving the transport device while sliding or in free-fall and before entering the collection vessel;
   checking the images to evaluate color quality of the preforms, wherein said checking includes identifying at least one preform properly positioned such that most or all of the preform is visible along a length of the preform and then evaluating the color quality of the identified at least one preform; and
   discovering defective preforms based on said evaluation of the color quality of the preforms.

2. The method of checking the color quality of preforms according to claim 1, wherein the image of the preforms is made while positioning the preforms in front of a projection screen or a plate.

3. The method of checking the color quality of preforms according to claim 2, wherein the preforms are able to slide over the plate as said slide.

4. The method of checking the color quality of preforms according to claim 2, wherein the projection screen or the plate have a color having a good contrast to the color of the preforms.

5. The method of checking the color quality of preforms according to claim 2, wherein the projection screen or the plate are at least partially transparent.

6. The method of checking the color quality of preforms according to claim 2, wherein attachment means are provided with which the projection screen or the plate can be positioned.

7. The method of checking the color quality of preforms according to claim 2, wherein the at least one portion of the plate is curved in at least one direction.

8. The method of checking the color quality of preforms according to claim 7, wherein the plate is curved in such a way that at least one channel for the sliding preforms is formed in the plate.

9. The method of checking the color quality of preforms according to claim 2, wherein the plate is perforated.

10. The method of checking the color quality of preforms according to claim 1, wherein a plurality of images are evaluated in order to determine a defective series of preforms.

11. The method of checking the color quality of preforms according to claim 1, wherein the preforms are illuminated by means of at least one lighting fixture when making the image.

12. The method of checking the color quality of preforms according to claim 11, wherein the at least one lighting fixture is positioned in such a way that the preforms are illuminated from behind with respect to the imaging device.

13. The method of claim 1 wherein the imaging device consists of a camera.

14. A system of checking the color quality of manufactured bottle preforms, comprising:
   a transport device for transporting preforms into a collection vessel;
   an imaging device for making an image of the preforms;
   a computer to which this image is transmitted for checking;
   wherein the transport device is positioned and arranged relative to the collection vessel such that the preforms are able to be led into the collection vessel unsorted upon leaving the transport device such that the preforms are sliding on a slide or in free-fall;
   wherein the image is made as the preforms are lead unsorted upon leaving said transport device and before entering the collection vessel, while sliding or in free-fall; and
   wherein the image is processed by the computer in such a way that the color quality of the preforms is checked and defective preforms are discovered, wherein said checking is carried out by image processing software that identifies at least one preform properly positioned such that most or all of the preform is visible along a length of the preform and then evaluating the color quality of the identified at least one preform.

15. The system of checking the color quality of preforms according to claim 14, wherein a projection screen or a plate is provided, wherein the image of the preforms is made while positioning the preforms in front of said projection screen or said plate.

16. The system of checking the color quality of preforms according to claim 15, wherein the preforms are able to slide over the plate as said slide.

17. The system of checking the color quality of preforms according to claim 15, wherein the projection screen or the plate has a color having a good contrast to the color of the preforms.

18. The system of checking the color quality of preforms according to claim 15, wherein the projection screen or the plate is at least partially transparent.

19. The system of checking the color quality of preforms according to claim 15, wherein attachment means are provided with which the projection screen or the plate is able to be positioned.

20. The system of checking the color quality of preforms according to claim 15, wherein the plate is perforated.

21. The system of checking the color quality of preforms according to claim 15, wherein at least a portion of the plate is curved in at least one direction.

22. The system of checking the color quality of preforms according to claim 21, wherein the plate is curved in such a way that at least one channel for the sliding preforms is formed in the plate.

23. The system of checking the color quality of preforms according to claim 14, wherein a lighting fixture is provided by means of which the preforms are able to be illuminated when making the image.

24. The system of checking the color quality of preforms according to claim 23, wherein the at least one lighting fixture is positioned behind the projection screen or the plate so that the preforms are able to be illuminated from behind with respect to the imaging device.

25. The system of checking the color quality of preforms according to claim 14, wherein a plurality of images are able to be evaluated in order to determine a defective series of preforms.

26. A method of checking the color quality of, manufactured bottle preforms, comprising:
    transporting the preforms by a conveyor belt toward a collection vessel;
    leading the preforms in an unsorted way into the collection vessel upon leaving the conveyor belt such that the preforms are sliding on a slide or in free-fall;
    forming an image of the preforms with a camera, said method being without using moving illumination, wherein the image is made as the preforms are lead in the unsorted way upon leaving the conveyor belt and before entering the collection vessel, while sliding or in free-fall;
    transmitting the image to a computer; and
    processing the image by the computer in such a way that the color quality of the preforms is checked and defective preforms are discovered, wherein said checking is carried out by image processing software that identifies at least one preform properly positioned such that most or all of the preform is visible along a length of the preform and then evaluating the color quality of the identified at least one preform.

27. A system of checking the color quality of preforms intended for the manufacture of containers, consisting of:
    a conveyor belt for transporting preforms toward a collection vessel;
    a camera for making an image of the preforms;
    a computer to which the image is transmitted;
    wherein the conveyor belt is positioned and arranged relative to the collection vessel such that the preforms are able to be led into the collection vessel unsorted upon leaving the conveyor belt such that the preforms are sliding on a slide or in free-fall;
    wherein the image is made as the preforms are lead unsorted upon leaving said conveyor belt and before entering the collection vessel, while sliding or in free-fall; and
    wherein the image is processed by the computer in such a way that the color quality of the preforms is checked and defective preforms are discovered.

* * * * *